US006724923B2

(12) United States Patent
Ma et al.

(10) Patent No.: US 6,724,923 B2
(45) Date of Patent: Apr. 20, 2004

(54) AUTOMATIC COIL SELECTION OF MULTI-RECEIVER MR DATA USING FAST PRESCAN DATA ANALYSIS

(75) Inventors: Jingfei Ma, Waukesha, WI (US); Guosheng Tan, Waukesha, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 532 days.

(21) Appl. No.: 09/681,473

(22) Filed: Apr. 13, 2001

(65) Prior Publication Data

US 2002/0186870 A1 Dec. 12, 2002

(51) Int. Cl.$^7$ .................................................. G06K 9/00
(52) U.S. Cl. ...................... 382/131; 382/274; 382/264; 382/132; 382/218; 600/410
(58) Field of Search .................... 382/131, 132, 382/172, 274, 209, 218, 264; 128/898, 922; 356/39; 703/2; 377/10; 600/422, 420, 410; 324/309, 307; 345/12, 20, 63, 77; 335/301; 250/282, 455, 205; 348/251, 254

(56) References Cited

U.S. PATENT DOCUMENTS

| | | | |
|---|---|---|---|
| 5,138,260 A | | 8/1992 | Molyneaux et al. |
| 5,414,358 A | * | 5/1995 | Eilenberg et al. ........... 324/309 |
| 5,495,849 A | * | 3/1996 | Hayashi et al. ............. 600/409 |
| 5,568,051 A | * | 10/1996 | Yamagata .................... 324/318 |
| 5,594,849 A | * | 1/1997 | Kuc et al. .................... 345/632 |
| 5,622,686 A | * | 4/1997 | Gordon et al. .............. 424/9.32 |
| 5,785,042 A | * | 7/1998 | Kao ............................. 600/410 |
| 6,134,465 A | | 10/2000 | Frederick et al. |
| 6,157,192 A | | 12/2000 | Cordes |
| 6,223,065 B1 | * | 4/2001 | Misic et al. ................. 600/410 |
| 6,294,972 B1 | * | 9/2001 | Jesmanowicz et al. ...... 335/301 |
| 6,320,378 B1 | * | 11/2001 | Maier et al. ................. 324/307 |
| 6,326,786 B1 | * | 12/2001 | Pruessmann et al. ........ 324/312 |
| 6,448,770 B1 | * | 9/2002 | Liu et al. ..................... 324/307 |
| 6,476,607 B1 | * | 11/2002 | Dannels et al. .............. 324/309 |
| 6,486,671 B1 | * | 11/2002 | King ............................ 324/307 |
| 6,597,936 B1 | * | 7/2003 | Liu et al. ..................... 600/420 |
| 6,597,937 B2 | * | 7/2003 | Liu et al. ..................... 600/420 |
| 6,639,211 B1 | * | 10/2003 | Anand et al. ................ 250/282 |
| 2002/0143504 A1 | * | 1/2002 | Jensen ............................ 703/2 |
| 2002/0021128 A1 | * | 2/2002 | Kuhara ........................ 324/309 |
| 2002/0040185 A1 | * | 4/2002 | Atalar et al. ................. 600/423 |

FOREIGN PATENT DOCUMENTS

| | | |
|---|---|---|
| EP | 91309248.2 | 5/1992 |
| WO | PCT/US99/07854 | 10/1999 |

OTHER PUBLICATIONS

Schaffter, et al., Fast H Spectroscopic Imaging Using a Multi–Element Head Coil Array, Magnetic Resonance in Medicine, vol. 40, 1998, pp. 185–193.

* cited by examiner

Primary Examiner—Timothy M. Johnson
Assistant Examiner—Barry Choobin
(74) Attorney, Agent, or Firm—Ziolkowski Patent Solutions Group, LLC; Michael A. Della Penna; Carl B. Horton

(57) ABSTRACT

Automatic coil selection is based on determining an index gauge for a corresponding k-space data line acquired for each preselected coil during a prescan. Reliance on manual coil selection and markers is eliminated by adaptively determining the coils of an MR system that produce a preferred sensitivity to a desired field-of-view (FOV). The fast scan data is used to determine those coils most sensitive to the FOV and reject coil(s) least sensitive. Using only data acquired with the most sensitive coils, SNR is increased and unwanted artifacts are reduced in the final data acquisition and image reconstruction. Through automatic and adaptive selection/deselection, the invention reduces the susceptibility to human error, and therefore results in higher quality images.

32 Claims, 5 Drawing Sheets

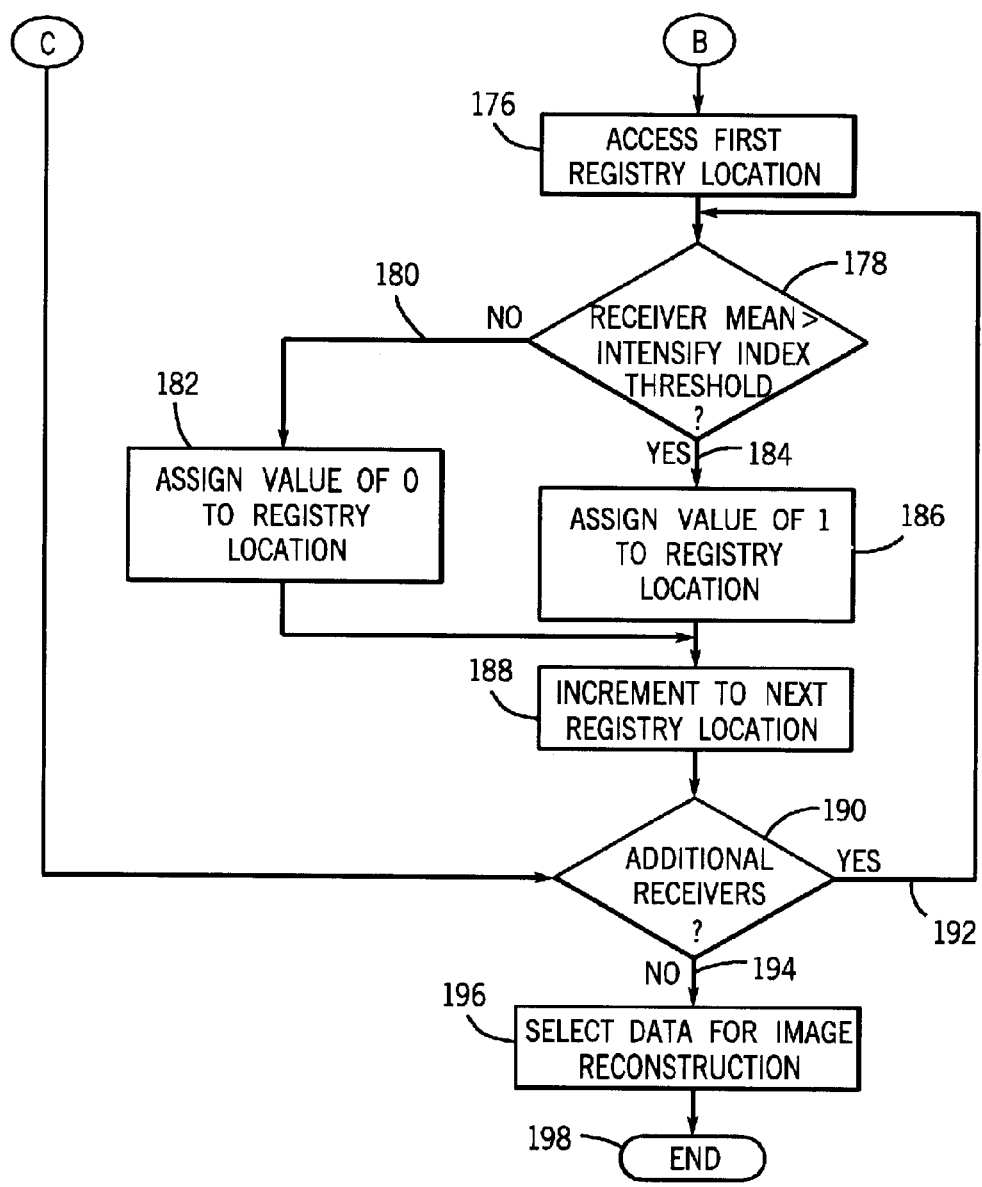

AUTOMATIC COIL SELECTION OF MULTI-RECEIVER MR DATA USING FAST PRESCAN DATA ANALYSIS

BACKGROUND OF INVENTION

The present invention relates generally to MR data acquisition and, more particularly, to a method and system for imaging with adaptive automated coil selection of a multi-coil imaging receiver assembly in a medical imaging device.

Diagnostic imaging devices, such as magnetic resonance (MR) scanners, can acquire imaging data using a series of receivers. Further, improved imaging devices can employ a coil assembly of phased array coils to acquire the imaging data over a desired imaging field-of-view (FOV). Phased array coils are often used because they yield a higher signal-to-noise ratio (SNR) and increased spatial coverage over the desired FOV. In these known imaging systems, imaging data acquired from each phased array coil is combined to form a final diagnostic image. Despite the implementation of phased array coils, reconstructing an image from the combination of the imaging data from all, or too many, of the phased array coils can produce ghosting in the final image from unwanted noise and artifacts.

Typically, these unwanted artifacts result from the acquisition of data from a phased array coil assembly that dimensionally exceeds the desired FOV of a subject, i.e., a medical patient. For example, in a known MR system that utilizes a coil assembly with six phased array coils, it is customary to utilize four of the six coils during a spinal imaging examination. However, in some spinal exams, the imaging FOV can be covered with only two or three coils to acquire sufficient data to produce a complete image. As a result of using the additional and unnecessary coils, noise and artifacts insensitive to the selected FOV are often included in the final image and result in undesirable ghosting in the final image. To reduce the noise and unwanted artifacts, it is desirable to use only those coils that are sensitive to the desired FOV.

Known systems seek to maintain sensitivity of the FOV by permitting manual selection of coils based upon patient positioning and other positioning tools prior the imaging session. Essentially, in these known diagnostic systems an MR operator or technician manually deselects coils so that these deselected coils do not acquire data during the imaging scan or, alternatively, specifically excludes data from arbitrary coils that are acquired during scanning from final image reconstruction on a trial and error basis. To properly deselect the appropriate coils, the operator must know exactly which coils to deactivate prior to the diagnostic scan, which is a difficult and time consuming task, and often requires guess work. The task of properly selecting the coils is exaggerated by the fact that the patient and patient table can frequently change positions during an imaging session. Further, deselection of the proper coils is a cumbersome task and one prone to human error that could result in requiring a total rescan. To require the operator to repeatedly deselect coils with each new patient and/or table position only increases the difficulty of deselecting the appropriate coils. Further, with multi-slice imaging techniques it would be necessary for the operator to deselect different coils during the imaging session—a daunting task in operator-based selection.

Attempts to automate coil selection have, in fact, not been made completely automatic. For example, in one approach the coils are selected only after requiring a system operator to furnish the scanner with 2–3 parameters that are based on the positioning of a landmark, or reference mark, placed on the subject at some known distance from isocenter. Such a system requires accurate placement of the landmark, or requires a measurement of the distance between the landmark and isocenter, and that measurement must be input into the system together with a dimension of the field-of-view between a pair of boundary limits, relative to the isocenter. Further, after the operator inputs the necessary parameters, some such known systems utilize conventional logic circuits together with a lookup table to select or deselect certain coils. Other known systems use a pilot scan, or prescan, to acquire parameters of a selected slice or imaging sequence and compare these properties to properties of the coil array that are stored in a lookup table. Not only do these systems rely on static data, they are subject to human error and/or require additional hardware configurations, and in the case of using markers, the images have to either be manually gridded or additional time and resources are expended on automatic gridding if the marker is machine identifiable. Examples of two coil selection systems include U.S. Pat. Nos. 5,138,260 and 6,134,465. Although such systems have functioned adequately, it would be desirable and advancement in the art, to design a fully automated system that does not rely on manual intervention, lookup table, and/or landmarks.

It would therefore be desirable to design a method and system to fully automate coil selection of an imaging device, or data from specific coils, to increase FOV sensitivity and clarity for multi-channel phased array imaging. It would similarly be desirable to design a method and system to determine phased array coil positions adaptively using an on-the-fly index gauge determination that is not dependent on a status lookup table, thereby facilitating selection of coils for image reconstruction with reduced artifacts.

SUMMARY OF INVENTION

This invention includes a method and system that is an adaptive and full-automated coil selection technique that overcomes the aforementioned drawbacks. The present invention facilitates image reconstruction with an increased signal-to-noise ratio and reduced artifact presence without manual selection of specific coils, without the use of reference marks and landmarks, and without using look-up tables. Through automatic selection and/or deselection of coils, the present invention discriminates between coils in an imaging field-of-view (FOV) based on an index gauge. Using imaging data from those coils with the best sensitivity within the FOV enables reconstruction of a final image with reduced noise and reduced artifacts from the image. The present invention implements automatic selection or deselection of coils based on an adaptive and dynamic analysis rather than reliance on manual selection, operator inputs, and/or landmark placement processes often prone to human error and requiring additional hardware.

In one embodiment of the present invention, preliminary scanning data is acquired during an initial fast scan. With a fast scan, a limited number of k-space data lines are acquired and sampled. By employing a fast scan, the present invention allows for a preliminary analysis to be completed to determine those phased array coils most sensitive to a FOV before acquiring a full set of imaging data. Typically, a fast scan or preliminary scan requires less time to complete than a full reconstruction imaging scan. After the preliminary imaging data is acquired during the fast scan, the imaging data is analyzed and evaluated to determine which coils to activate during a full reconstruction imaging session. Analyzing and evaluating the preliminary scan to determine which coils to activate or deactivate during a full imaging session may be carried by adaptively determining an index gauge for at least one k-space data line acquired for each coil, comparing the index gauge on-the-fly, and then automatically selecting or deselecting a number of MR coils to activate for image data acquisition based on the comparison of the dynamically determined index gauge.

In accordance with one aspect of the present invention, a method to automatically select/deselect coils, for image reconstruction, using prescan image data of an MRI device having a number of coils is provided. The method includes the step of initializing a fast scan to acquire k-space data sets via a number of phased array coils. The number of k-space data sets includes at least one k-space data line for each of a plurality of MR coils. In evaluating the k-space data, an index gauge is adaptively determined for at least one k-space data line acquired for each coil. A threshold value is dynamically found for a comparison of the index gauges. In this manner, a number of MR coils can be automatically selected, or deselected, based on the index gauge comparison.

In a preferred embodiment, the index gauge can include an intensity value extracted from the k-space data. In this case, the intensity values are then arranged into an intensity profile that enables identification and selection of a number of phased array coils to activate for final imaging data acquisition. After the coils to be activated have been selected, or the coils to be inactive are deselected, full image data can be acquired to reconstruct an image with increased SNR.

In accordance with another aspect of the invention, a computer program is disclosed that includes instructions to cause a computer program to acquire and analyze prescan data acquired from activating a number of phased array coils during a preliminary MR scan, and then extract a relative intensity of the data for each coil. Based on the relative intensity of each coil, a number of phased array coils is selected, or deselected, for activation to acquire data during a reconstruction imaging scan. Accordingly, the selection or deselection of the coils is made dynamically and without operator input or markers.

In accordance with yet another aspect of the present invention, an MRI apparatus is disclosed having a magnetic resonance imaging system having a plurality of gradient coils positioned about the bore of a magnet to impress a polarizing magnetic field and an RF transceiver system. The MRI apparatus further includes an RF switch controlled by a pulse module to transmit RF signals to a phased array coil assembly to acquire the MR images. The MRI apparatus also includes a computer programmed to initialize a fast MR scan using a plurality of coils in the phased array coil assembly and acquire fast scan imaging data of an image FOV. The fast scan imaging data includes at least one k-space line of data for each of the plurality of coils in the phased array coil assembly. The computer is also programmed to determine a relative position of each of the plurality of coils with respect to the desired FOV based only on the at least one k-space line of data. The computer can then select and initialize only a number of the plurality of coils for image acquisition and reconstruction based on the relative positions of each coil in order to optimize SNR in the desired FOV.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention. In the drawings:

FIGS. 3–5 taken together show a flowchart for selecting coils of an MRI system in accordance with the present invention.

DETAILED DESCRIPTION

Figure 1:
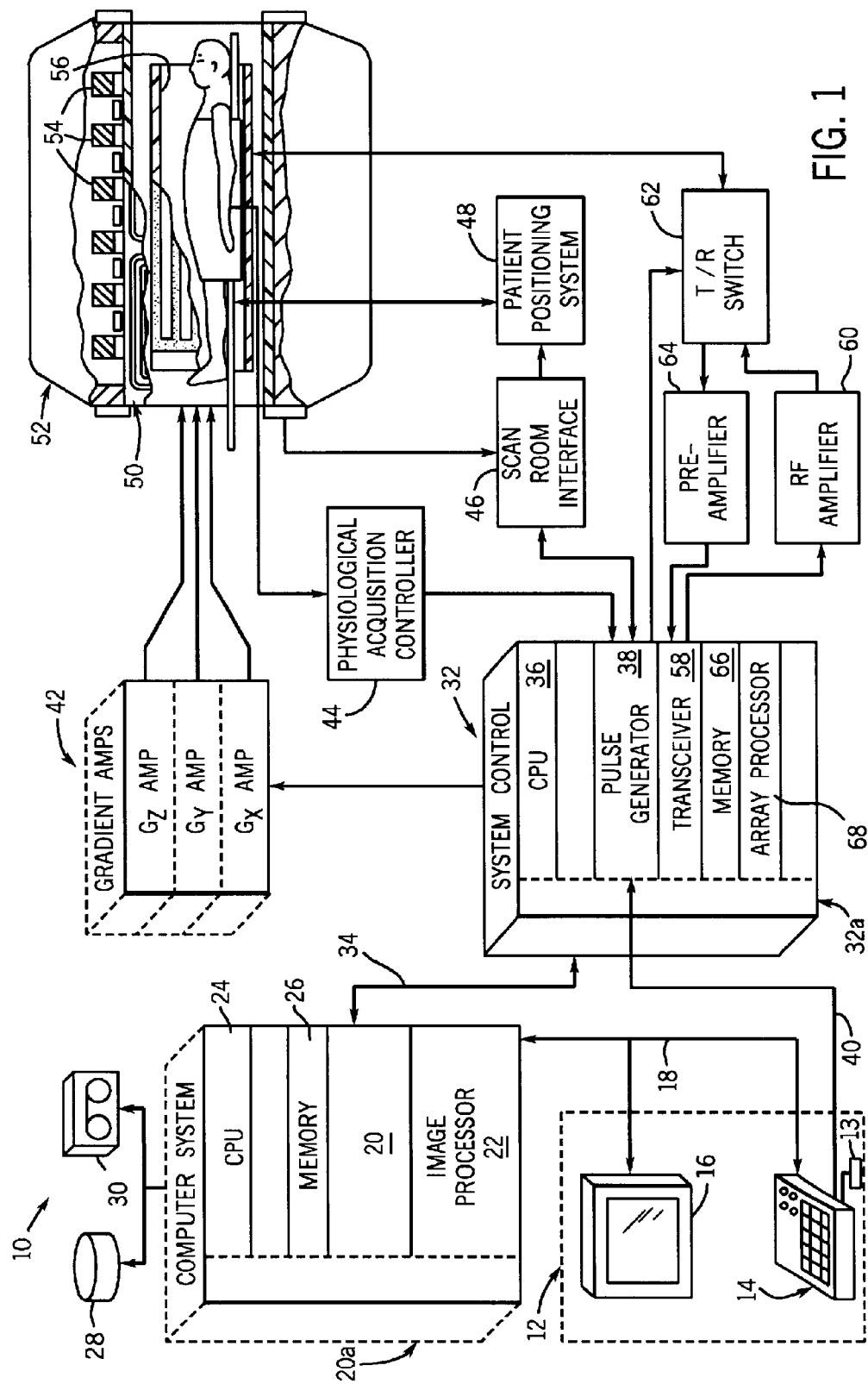
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56, which can include a phased array coil assembly. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

Figure 2:
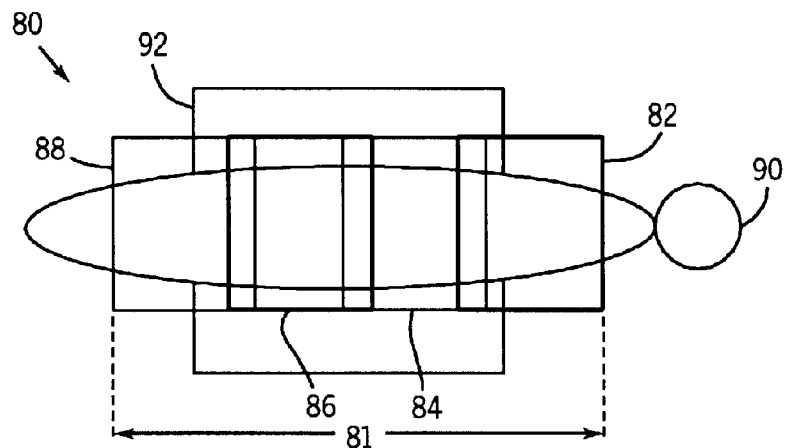
FIG. 2 is a schematic representation of a multi-coil MRI system for use with the present invention.

Shown in FIG. 2 is a representation of an imaging area resulting from implementation of a multi-coil MRI system, such as that generally shown in FIG. 1. For illustration purposes, the imaging area 80 results from a four-coil selected MRI device. One of ordinary skill in the art, however, will appreciate that the invention set forth herein is applicable to any multi-coil imaging device. The imaging area 80 shown in FIG. 2 includes four separate yet overlapping coil coverage areas 82, 84, 86 and 88. Each coil coverage area 82–88 is dimensionally equivalent and represents an equally proportioned data acquisition region of the patient 90. The combination of the coil coverage areas 82–88 results in a sum coil coverage area 81. Within the sum coil coverage area 81 is a desired image field-of-view (FOV) 92, that can span across several individual coil coverage areas 82–88. The image FOV 92 can be dimensionally identical to the sum total of the coil coverage areas 82–88, but, in many situations, such as shown in FIG. 2, the image FOV may be less than the sum of the coil coverage areas 82–88. When the sum coil coverage area 81 exceeds the image FOV 92, one or more of the coils of the MRI system often acquire imaging data outside the desired FOV 92. Further, as shown in FIG. 2, since portions of coil coverage areas 82 and 88 lie outside the desired FOV 92, imaging data from these areas may have undesirable effects, such as poor field homogeneity, severe eddy currents, and low SNR.

To reduce noise in a final reconstructed MR image and to help eliminate unwanted artifacts, a technique to fully automate coil selection is disclosed. To produce an artifact reduced reconstructed image with increased SNR, the system includes a coil receiver assembly having a series of phased array coils, such as those found on a GE 1.5T Signa® System. As indicated previously, the MR imaging signals detected by the receiver coil assembly are digitized and transferred to a memory location within the MRI system of FIG. 1. Data is organized in sets corresponding to each coil from which it was received. Using the stored MR image data, a computer program having a set of instructions causes a computer to determine an index gauge for each MR image data set. The system provides for the computer to determine from which phased array coil a particular image data set was acquired. By recognizing from which coil a particular image data set pertains, the computer is able to adaptively and dynamically select or deselect those coils and their corresponding images that should be used for final image reconstruction based on the index gauge. It is noted, depending on context, one may either "select" a subset of coils, or "deselect" coil(s). Since the end result is the same, which term is used is irrelevant. Therefore, select and deselect are used herein interchangeably and are hereby defined to have substantially the same meaning.

An index gauge is constructed to sort out all the active coil elements corresponding to a distance to the selected FOV. As opposed to attempting to determine coil positions explicitly, either manually or using some positional markers for coil selection, the present invention capitalizes on a theory that the closer the coil element is concentrated within the selected FOV, the higher sensitivity it will have to the same region of interest. Therefore, in one embodiment, a convenient index gauge is selected as the total intensity of each image, which will be further explained hereinafter. In general, the present invention is based on dynamically extracting relative sensitivity information for each coil from the individual images produced, or from the raw data in a rescan, to differentiate data on-the-fly. Conversely, the prior art relies on coil selection that is dependent on patient and a landmark positioning, obtaining and inputting certain parameters by the operators prior to imaging, and/or using coil markers and a prescan image to guide coil selection with predetermined parameters or properties stored in a lookup table.

Preferably, in one embodiment the disclosed technique achieves fully automated coil selection by using information contained in a set of intermediate images. These intermediate images are the individual component images from each separate coil before their combination into a final image. If desired, the information derived from these intermediate images can be combined with specific coil geometries and physical configurations. However, it is contemplated that this additional step would be optional, and the invention is not so limited. The intermediate image from the i-th coil is given as:

$$I_i(x,y) = S_i(x,y) M(x,y); \quad \text{(Eqn. 1)}$$

where $I_i(x,y)$ represents the intermediate image from the i-th coil, $S_i(x,y)$ represents the spatial sensitivity in the i-th coil in the FOV, and $M(x,y)$ represents the spin density, including the proper spin relaxation, of the object to be scanned within the selected FOV.

In one embodiment of the invention, the coils to be included in final image reconstruction are selected or deselected based on the relative integrated image intensity of each MR image detected by the phased array coil assembly. With this approach, a convenient index gauge ($G_i$) is the total intensity of each image, which is proportional to the integrated coil sensitivity over the FOV under the approximation of a constant spin density, as given as:

$$G_i = \sum_{(x,y)} |S_i(x,y) M(x,y)| \approx M_o \sum_{(x,y)} |S_i(x,y)|, \quad \text{(Eqn. 2)}$$

where $G_i$ is the index gauge and $M_o$ is the approximate constant spin density. The summation is over the spatial pixels in the selected FOV. Based on the image intensity of the MR images, the invention automatically deselects the coil(s) producing images with the least desirable image intensity for final image reconstruction.

To determine which coils and their respective images to exclude from final imaging, the present invention contemplates the exclusion of images having an intensity less than an intensity threshold value. The threshold value can depend on the coil geometry and the particular imaging parameters selected by the operator and will be described further with reference to FIG. 3. Generally though, the intensity threshold value is the product of a maximum mean value and the number of receiver coils preselected. Preferably, the intensity threshold value is determined on-the-fly based on the index gauge for each of the coils. In this manner, the coils are compared to one another dynamically instead of some predetermined parameter. It is noted that with constant spin density (M(x,y)), the image intensity for each detected MR image is equal to the integrated coil sensitivity over the chosen FOV, which should decrease as the distance between the phased array coil and the FOV increases. Further, in the practical case where there is a presence of spatial variation in the spin density, the relationship between image intensity and coil distance from the selected FOV holds because the sensitivity values of different phased array coils are weighted by the same spin density value or profile.

The present invention further contemplates an alternative embodiment for determining which images to include and/or exclude from final image reconstruction. This alternative embodiment, as set forth below, may be used in place of or in conjunction with the technique heretofore discussed. To enable adaptive selection of phased array coils and the data for reconstruction, the technique includes projecting the intensity of each MR image onto a major axis of the receiver coil assembly. This projection of image intensity onto a map of the receiver coil assembly allows the computer to determine those phased array coils that acquired the most pronounced images. Those pronounced images, i.e., those images with the highest intensity, reveal and normally correspond to those phased array coils most sensitive to the selected FOV.

Rather than determining phased array coil position from an intensity profile fit, the computer may be programmed to alternatively determine a center of mass of the images based on image intensity. Those MR images with concentrations near the center of mass indicate which phased array coils are most significantly sensitive to the desired FOV. In a further embodiment, the computer may be programmed to find the peak location of the intensity profile along the major axis of the phased array coils. The peak image intensity location reveals which coils are most sensitive and are within the selected FOV. In those situations where the intensity profile, or alternatively the center of mass or peak image intensity position, cannot be reliably determined because a phased array coil lies outside the selected FOV, the phased array coil position may be determined from the positioning of the phased array coils located within the FOV. Determination of a coil position outside the FOV is possible because the relative coil distance and the relative coil position for a given phased array coil is fixed. Once the coil position is determined relative to the selected imaging FOV, the invention automatically selects which coils are to be included and thus, those coils to be excluded from final image reconstruction.

The index gauge ($G_i$) calculation described with reference to Eqn. 2 is just one example for finding an index gauge, such as the total intensity of each image. Other index gauges are contemplated and within the scope of the present invention. Another example of a index gauge can be designed without assuming a constant spin density such as:

$$G_i = \sum_{(x,y)} \left( |I_i(x,y)| / \sum_i |I_i(x,y)| \right) = \sum_{(x,y)} \left( |S_i(x,y)| / \sum_i |S_i(x,y)| \right) \quad \text{(Eqn. 3)}$$

where $S_i(x,y)$ is a spatial sensitivity of an i-th MR coil of an N-coil phased coil array, $I_i(x,y)$ is a total intensity obtained from central k-space data for each MR coil, and wherein the summation is over all spatial pixels in a desired FOV. It is also noted that the index gauge can be determined before image reconstruction because the total intensity is within the central portion of the k-space data. Once the intermediate images are sorted according to their respective index gauge, inclusion into the final image can be based on either setting a threshold to the gauge index, or on selecting a number of coils for a given protocol.

Figure 3:
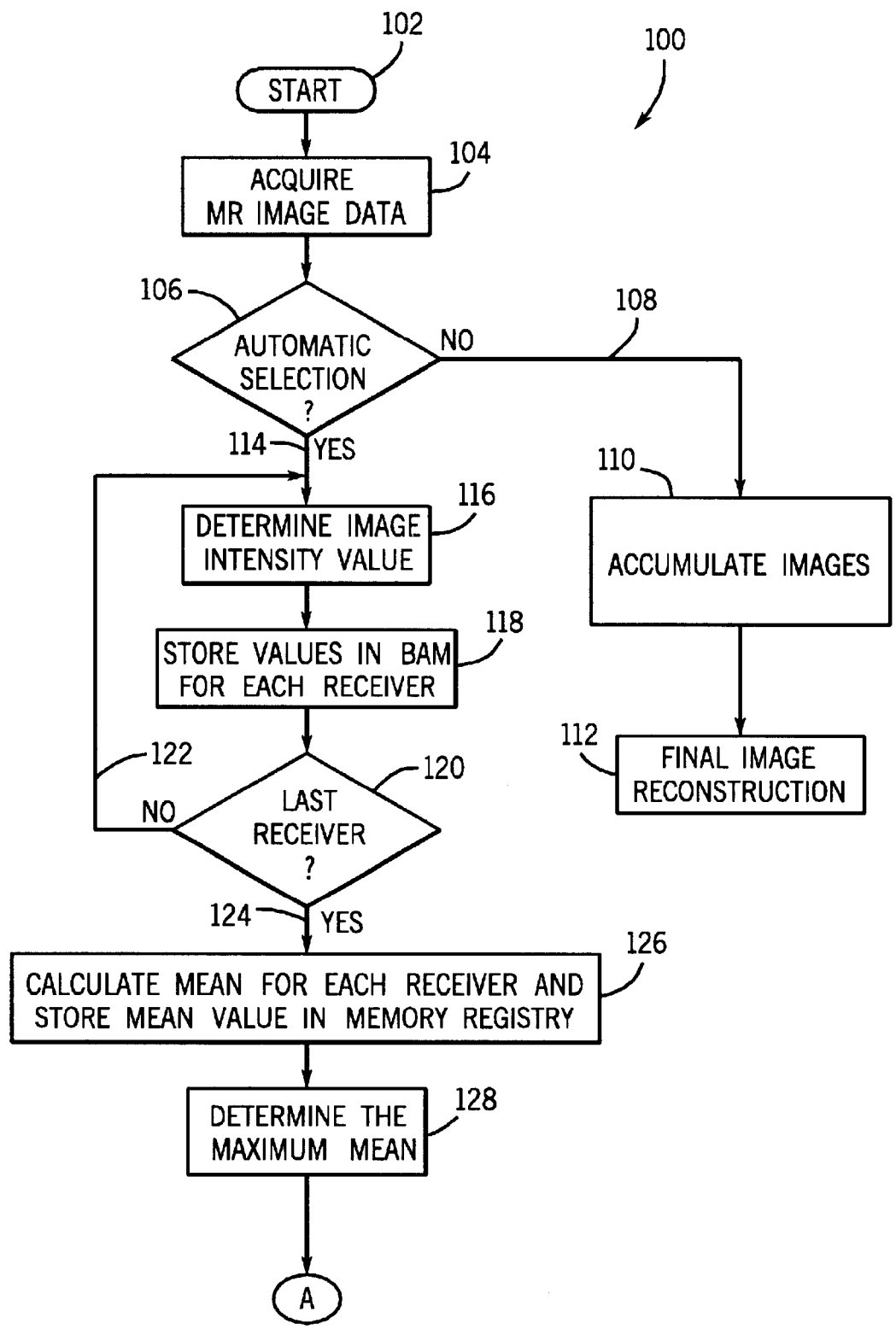
Figure 4:
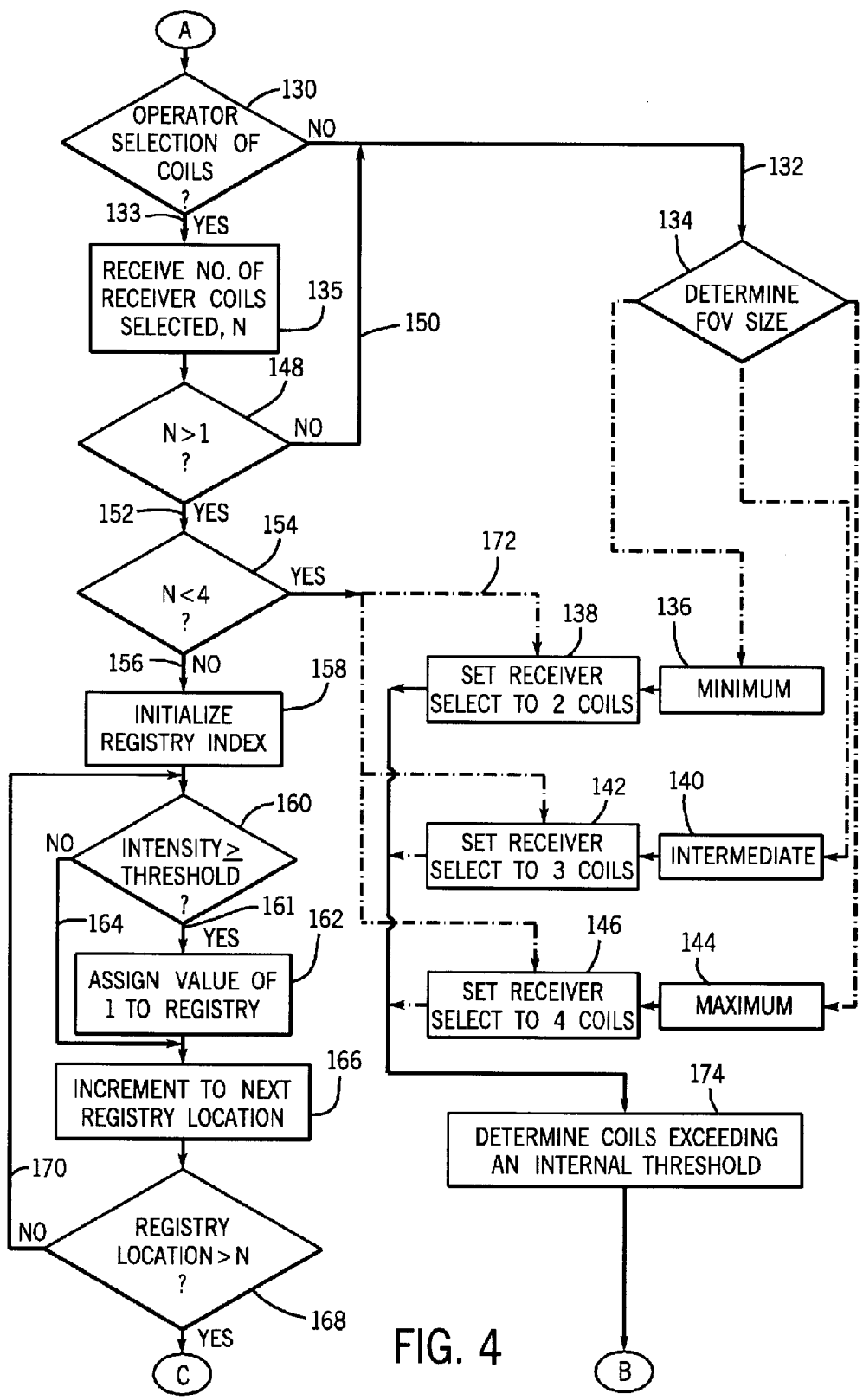

Referring to FIGS. 3–5, the present invention includes an algorithm 100 for automatically and dynamically selecting coils and/or data for image reconstruction that is adaptive to many configurations without using landmark hardware and lookup tables with predefined data therein. The invention further contemplates a computer program having a set of instructions that when executed causes one or more computers to carry out the steps of the algorithm, or method, as will also be disclosed with reference to FIGS. 3–5. The specific embodiment described with reference to FIGS. 3–5 is one in which complete MR data is acquired for each coil preselected. That is, as an example, if a six element phased array coil is used to image the spine, typically only the middle four elements are used, and it is those four elements that are preselected. In one particular embodiment, complete image data is acquired for all the coil elements, including the coil elements that may not be as sensitive to the selected FOV as the others. In this case, if data from the coil elements that are not as sensitive to the selected FOV were used in final image reconstruction, they would contribute to the introduction of additional noise and render the final image prone to artifacts since these coils may be sensitive to spatial regions beyond the design volume of the scanner system. As previously alluded to, in one embodiment, after complete data acquisition from all preselected coil elements, the data can be processed into individual images before reconstruction into a single image. With the coil selection algorithm of this embodiment, the image from the least sensitive coil element(s) is rejected automatically based on the index gauge. In another embodiment, a fast prescan is conducted to acquire and analyze only central k-space data. In this case, the coil(s) that produce the least desirable index gauge are eliminated from acquiring complete k-space data for image reconstruction. Although the description of the algorithm shown in FIGS. 3–5 is primarily focused on the former, one skilled in the art will readily recognize an implementation of the latter taken together with the detailed description of the invention.

Referring first to FIG. 3, the aforementioned process 100 begins at 102 with the acquisition of MR image data 104 or a fast prescan to acquire the raw central k-space data, as previously outlined. After acquisition of the MR images at 104, the operator of the MRI system may choose whether to implement the automatic coil selection technique and system of the present invention at 106. If the operator chooses not to implement the automatic coil selection technique 106, 108, MR imaging data from each phased array coil of the coil assembly is accumulated at 110 and used to reconstruct a final image at 112. However, if the operator elects to implement the automatic coil selection system 106, 114, then an image intensity value is determined at 116 for each acquired data set. This option would be provided earlier if the prescan embodiment is implemented.

Beginning at 118, the image intensity values determined at 116 are arranged to correspond to a particular receiver coil of the coil assembly whether acquired with the fast prescan or if full image data is acquired. Organizing the image intensity values in this manner allows the system to determine a mean intensity value for each receiver coil. As the image intensity values are organized, the intensity values associated with a particular receiver are stored in bulk access memory (BAM) of the MRI system. It is then determined at 120 if the image intensity values for the images associated with each receiver coil of the coil assembly have been stored in memory of the MRI system. If all the image intensity values associated with each receiver coil have not been received 120, 122, the process returns to step 116 to determine and store in memory the image intensity values for any remaining receiver coils. Once the image intensity values associated with the last receiver have been stored in memory and verified at 124, a mean value is determined and stored at 126 for each receiver coil based on the image intensity values associated with each particular receiver coil. Using the mean values determined at 126 for each receiver coil, a maximum or total mean value is determined at 128. The maximum or total mean value determined at 128, will be utilized in establishing a threshold value that must be exceeded before those images acquired by a particular coil are included in final image reconstruction.

Continuing to FIG. 4, the present invention affords the operator several options to automatically select phased array coils and their corresponding MR images for final image reconstruction. However, the operator is not required to input any parameters to execute the automated coil/data selection. The options merely allow the operator to opt-out of a fully automated selection. The operator can opt to a semi-automatic selection at 130 where the operator selects a desired number of receiver coils to be used for data acquisition or final image reconstruction. If the operator chooses to allow a fully automated selection of coil data to use, or select the number of coils 130, 132, then the number of coils used for image reconstruction will be based solely on the technique of the present invention after determining a desired FOV size at 134. The technique provides an initial division of the coils with a determination of a minimum FOV 136, an intermediate FOV 140, and a maximum FOV 144. As an example, in a typical MRI system, each phased array coil is 120 mm in length. Therefore, in a preferred embodiment, a minimum FOV size 136 corresponds to an FOV ranging from 0 to 180 mm in length. Further, in response to a finding of minimum FOV size 136, the technique automatically concludes at 138 that MR image data acquisition from two phased array coils are adequate to realize the minimum FOV. The present invention further contemplates an intermediate sized FOV 140 corresponding to an FOV ranging in 181–450 mm and requiring MR image data acquisition from three phased array coils 142 to fill an intermediate sized FOV. Additionally, a maximum FOV 144 may be determined and includes any FOV larger than 450 mm. To achieve a maximum FOV range of greater than or equal to 450, MR image data acquisition from four phased array coils 146 are necessary.

As indicated previously, the present invention contemplates operator intervention to manually choose the number of phased array coils to be used for final image reconstruction 130, 133. Under this option, the operator may select any number of coils ranging from one to the total number of coils in the MRI system 135, but not specific coils. After receiving the operator's number of receiver coils selection at 135, the technique determines if the number of coils selected is more than a single coil at 148. If not 150, the process proceeds to determine FOV size at 134 as previously discussed. If the operator identifies only one coil to be used in final image acquisition and reconstruction at 135, or does not select any coils, the process ignores such an invalid input and selects at least two coils for final image reconstruction. The system may provide operator feedback with a notice of the invalid input and an opportunity to correct the input. The steps for initially determining the number of coils to use during final image data acquisition and reconstruction for an operator selection of one, or no selection at all, are described with reference to steps 134–146 as previously discussed.

If the operator selects more than one receiver coil 148–152, the present invention determines at 154 if the number of coils selected is less than a maximum number of coils allowed for the acquisition, which is four as is shown in FIG. 2. If the number selected is not less than the maximum 156, a register index and/or counter is initialized to a value of zero at 158. Initializing the register index and/or counter to a value of zero at 158 assures that each receiver mean value stored in memory at 126 is properly evaluated. After the register index is initialized at 158, the receiver mean value stored in a first register position is called and compared at 160 to an intensity threshold value. The intensity threshold value represents a basis for determining which coils to exclude from image reconstruction.

Preferably, the intensity threshold value is the product of the maximum mean determined at 128, FIG. 3, and the number of receiver coils selected at 135. Moreover, the product is divided by 100 thereby yielding a percentage value. Empirical data suggests that an intensity threshold value of approximately 60–65% has been sufficient to exclude images from those coils that are least sensitive to the desired FOV. At 160, the receiver mean value for a first receiver mean is compared to the intensity threshold value. If the first receiver mean value is greater than or equal to the intensity threshold value 161, a value of one is assigned to the first receiver at 162. If the receiver mean value is less than the intensity threshold value 164, the register index is incremented by one at 166 thereby leaving a value of zero for the first phased array coil.

At 168, the method and/or computer program compares the current registry index with the total number of coils selected at 135. If the current registry index does not exceed the number of coils selected 170, the technique returns to step 160 and compares the receiver mean value of the next phased array coil to the intensity threshold value. Steps and/or acts 160–170 continue until each receiver mean value has been compared to the intensity threshold value and a proper register value, i.e., one or zero, has been appropriately assigned. Once each receiver mean value has been evaluated, the method and/or computer program proceeds along execution path C to step 190 of FIG. 5 as will be discussed shortly.

Referring back to step 154, FIG. 4, if the number of selected coils are, in fact, less than a maximum, in this case four, the method and/or computer program continues at 172. In a situation wherein the number of coils selected is greater than one but less than the maximum, the process will select and use the "best" coils for image data acquisition and reconstruction. That is, an operator selection of three coils for image reconstruction will be recognized by the process, but such a selection of three coils merely represents the total number of coils to be used as part of image reconstruction and not the specific three coils to be used. Determining the "best" coils to use 138, 142, 146 is done generally using the index gauge, and more particularly, using one of the techniques previously described, or any other technique to perform the task without additional operator input and landmarkers, and/or lookup tables.

Under all circumstances, except for a selection of a number of receiver coils in excess of the maximum, each receiver mean value will be compared to an internal, preselected threshold value determined at 174. This internal threshold value operates as an additional limiter of MR images or raw data acquisition to be included in the final reconstruction. For example, the process may recognize an internal threshold value of 45%. With this threshold value, each receiver mean value will be compared to this internal threshold value and each receiver mean value will be appropriately ranked. If the method and/or computer program automatically determines that three receiver coils are needed for the selected FOV or the operator identifies three as the desired number of coils to use, the "top" three receiver means will be considered for image reconstruction based on the internal threshold value.

Likewise, the internal threshold value operates to exclude images from receiver coils that otherwise may have been used for image reconstruction. For instance, an operator may request at 135 that two receiver coils be used for image reconstruction, however, only one of the receiver coils may have a receiver mean value that exceeds the internal threshold value. As a result, only data acquired from the one receiver coil will be used for final image reconstruction despite the operator's request that two receiver coils be considered.

After those coils having a receiver mean exceeding the internal threshold limit are determined at 174, a first registry location is accessed and set to zero at 176, FIG. 5. The first receiver mean corresponding to the first registry location is then retrieved and compared to an intensity index threshold value at 178. The intensity index threshold value may depend on hardware parameters and specifications. However, empirical data suggests that an intensity index threshold of approximately 60–65% of the total receiver mean can result in a final reconstructed image absent significant ghosting and noise. If the receiver mean associated with the first registry location does not exceed the intensity index at 180, then a value of zero is assigned to the receiving coil associated with that particular receiver mean 182, and that coil/data is rejected. If the receiver mean is greater than or equal to the intensity index 178, 184, a registry value of one is assigned to the receiver coil of the coil assembly at 186, and the corresponding coil/data is considered acceptable.

Once a value of zero or one has been appropriately designated to the current receiver coil, the method and/or computer program proceeds at 188 to the registry location corresponding to the next receiver coil of the coil assembly. At 190, the method and/or computer program determines if any additional receiver mean values need to be compared to the intensity index threshold. If so 192, the method and/or computer program loops back to step 178 and determines if the new current receiver mean exceeds the intensity index threshold and proceeds through steps 180–188 accordingly.

Once the last receiver mean has been compared and no additional receiver mean values are available 190, 194, the computer program and/or method continues to step 196 to select the MR data needed for image reconstruction. The selection of data for image reconstruction will be discussed in further detail with reference to FIG. 6. Once the selection of data and the final image is complete, the current method and/or computer program terminates at 198.

Figure 6:
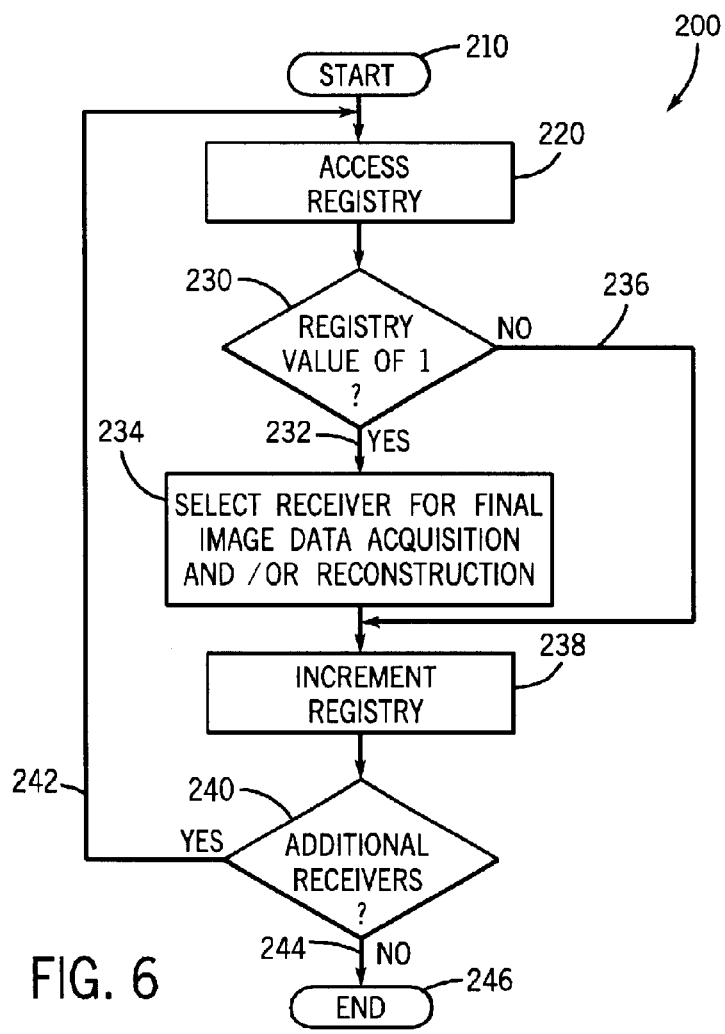
FIG. 6 is a flowchart to facilitate automatic coil selection in accordance with the present invention.

Referring now to FIG. 6, a flow chart representing the steps of a method and/or acts of a computer program in accordance with the present invention is shown to select data or select the coils for MR image reconstruction based on the registry values assigned to the respective coils of the coil assembly in accordance with the steps and/or acts of FIGS. 3–5. The method and/or computer program to select data or select the coils for image reconstruction 200 begins at 210 with the accessing of registry information at 220. The registry values are retrieved from memory and analyzed one at a time to determine which coils should have their respective MR images, or raw data, used for image reconstruction. A first registry value is retrieved and compared at 230 to a registry index value of one. If the registry index has a value of one and the first accessed registry value also has a value of one, the process continues at 232 and selects the receiver coil corresponding to the first registry value for final image data acquisition and reconstruction at 234. Conversely, however, if the registry value for the first receiver coil does not equal a registry index value of one 230, 236, then the process continues to step 238 without the receiver coil associated with the first registry value being included in the final image acquisition and reconstruction or in deselecting that coil for final image data acquisition. At 238, the process increments to the next registry location corresponding to the next receiver coil of the coil assembly. At 240, a determination is made if registry values for any additional receiver coils are available. If so 242, the process begins anew at step 220 for the new registry value. If no additional registry values need to be analyzed 244, selection of the receiver coils, or data to be used for final image acquisition and reconstruction terminates at 246 with each receiver coil having MR imaging data exceeding one or more intensity index thresholds included in the final image reconstruction, or selecting only those coils with prescan data that exceeds these specifications are activated for complete data acquisition.

Therefore, the present invention contemplates an adaptive method to automatically select MR data for image reconstruction that includes acquiring an image data set from each of a plurality of receiver coils and then determining an index gauge for each image data set. The index gauge is a representation of a spatial relationship between a given receiver coil and a desired FOV. The method next includes comparing the index gauges, and removing any image data set having an index gauge demonstrating a spatial relationship between the given receiver coil and the desired FOV that is less than optimal based on the comparison. The process also includes reconstructing an image from the remaining imaging data sets.

In another embodiment of the present invention, a method of automatically determining a subset of acquired data from a field-of-view of a receiver assembly that has a number of coils therein is disclosed. This method includes acquiring a number of images from a plurality of coils of an FOV and determining an image intensity for each of the number of images. The process also includes projecting the image intensity of each image onto a virtual access of the plurality of coils to create an intensity profile map. A subset of images is then selected based on the intensity profile map to reconstruct an image with reduced artifacts.

In accordance with yet another embodiment of the present invention, an MR imaging apparatus to acquire scanned images is provided. The MR imaging system further includes an RF transceiver system and an RF switch controlled by a pulse module to transmit RF signals to an RF coil assembly to acquire MR images. Receiver assemblies having a number of phased array coils are often used in magnetic resonance imaging systems. The coils are typically positioned about the bore of a polarizing magnet to impress a polarizing magnetic field. The apparatus includes a computer programmed to acquire an MR image from each coil of a multi-coil RF coil assembly across an image FOV and determining an intensity value for each MR image. The computer also determines an intensity value for each MR image and differentiates the MR images acquired from each coil based on the intensity values in order to discard any MR image having excess data acquired outside the image FOV. A final image can then be reconstructed with reduced artifacts by combining the remaining MR images.

Another embodiment of the invention includes a computer program having a set of instructions such that when executed by a computer causes the computer to acquire a set of imaging data includes a number of data frames, determine an intensity value for each data frame, and determine an intensity index from each intensity value. The program then forms a reconstruction data set that only includes the data frames having an intensity value exceeding the intensity index and reconstruction image from the reconstruction data that eliminates at least one data set being the least sensitive to the FOV.

An MR scanner is also disclosed that includes a means for acquiring an image data set from each of a plurality of receiver coils and a means for determining an index gauge for each image data set, wherein the index gauge represents a spatial relationship between a given coil receiver and a desired FOV. The MR scanner also has a means for removing any image data set having an index gauge demonstrating a spatial relationship between the given receiver coil and the desired FOV that is less than optimal based on the comparison. The scanner also includes a means for reconstructing an image from the remaining imaging data sets.

The present invention also contemplates a method to automatically isolate, for image reconstruction, scanned images of an MRI device having a number of phased array coils. The method includes the steps of acquiring, via the phased array coils, a number of imaging data frames including a number of k-space data sets and determining an intensity value for each imaging data frame. Next, an intensity profile is created and includes a map of the phased array coils designating the intensity values of the number of imaging data frames. From the intensity profile, a position of each phased array coil is obtained. The method further includes determining, from the position of each phased array coil, a reconstruction data set of imaging data frames from which to form a final reconstructed image.

In another embodiment of the present invention, as previously described, preliminary scanning data is acquired during a fast scan, or a prescan. In this embodiment, the technique is also adaptive and dynamic and does not rely on hardware landmarks, lookup tables, and operator input parameters for coil/data selection. After initializing a fast prescan in acquiring k-space data that includes at least one k-space data line for each of a plurality of MR coils, the technique includes adaptively determining an index gauge for at least one k-space data line acquired for each coil. The index gauges are compared to a threshold and based on the comparison, the process can automatically select/deselect a number of MR coils to activate for complete image data acquisition. By employing a fast prescan, the present invention allows for a preliminary analysis to be performed to determine which phased array coils are most sensitive to the desired FOV before acquiring a full set of imaging data.

The step of adaptively determining an index gauge includes extracting a relative intensity of each coil from the acquired k-space data, in a manner as previously described. The index gauge can be an intensity value of the k-space data line acquired in the fast prescan for each coil. In this case, the invention includes arranging the intensity values for the k-space data lines into an intensity profile, selecting a number of phased array coils to activate during final image data acquisition from the intensity profile, and acquiring image data during the final imaging data acquisition from only the phased array coils selected. It is noted that the index gauge can be determined before the image reconstruction because the total intensity is contained in the central portion of the k-space data. Accordingly, the fast prescan is focused at acquiring data in the central portion of the k-space.

The invention also includes a computer program having a set of instructions that, when executed by a computer, causes the computer to analyze prescan data acquired from activating a number of phased array coils during a preliminary MR scan and to extract a relative intensity of each coil from the prescan data. The program then determines a number of phased array coils to activate in order to acquire reconstruction imaging data during a reconstruction imaging scan from the relative intensity of each coil.

In one embodiment, the computer program profiles the relative intensity for each coil onto a map of a phased array coil assembly having a plurality of phased array coils capable of acquiring the prescan data and activates those phased array coils most sensitive to an imaging FOV. Alternatively, the computer program can cause the computer to integrate a coil sensitivity profile weighted by a spin density of a scanning subject over the FOV for each phased array coil to determine the relative intensity of each coil. The prescan data from a phased array coil that is analyzed, includes an intermediate image that can be expressed in accordance with Eqn. 1, and the relative intensity can be expressed as an index gauge ($G_i$) according to either Eqns. 2 or 3, or any similar equivalent index gauge that is not dependent upon hardware landmarks, operator input parameters, and/or lookup tables. The program also allows for on-the-fly calculation of a threshold value from the relative intensities to eliminate at least one coil with a lowest relative intensity.

Another embodiment of the present invention includes an MRI apparatus to acquire MR images. The MRI apparatus includes a magnetic resonance imaging system having a plurality of gradient coils positioned about the bore of a magnet to impress a polarizing magnetic field and an RF transceiver system. The MRI apparatus further includes an RF switch controlled by a pulse module to transmit RF signals to an RF coil assembly to acquire the MR images. The RF coil assembly includes multiple coils, such as a phased array coil assembly. A computer is provided and programmed to initialize a fast MR scan using a plurality of coils in the phased array coil assembly and acquire fast scan imaging data of a desired FOV. The fast scan imaging data includes at least one k-space line of data for each of the plurality of coils in the phased array coil assembly. The computer is further programmed to determine a relative position of each of the plurality of coils with respect to the desired FOV based only on the at least one k-space line of data acquired. The computer can then select and initialize a limited number of coils from the plurality of coils for image acquisition and reconstruction based on the relative positions of each coil in order to optimize SNR in the desired FOV. The various aforementioned techniques are used in determining the relative position of each of the plurality of coils. In this manner, the coils selected more accurately fit the FOV and extraneous data that can have adverse effects on image reconstruction is not acquired.

The present invention has been described in terms of the preferred embodiment, and it is recognized that equivalents, alternatives, and modifications, aside from those expressly stated, are possible and within the scope of the appending claims.

What is claimed is:

1. An adaptive method to automatically select/deselect coils in an MRI device for improved image reconstruction comprising the steps of:
   initializing a fast prescan and acquiring k-space data that includes at least one k-space data line for each of a plurality of MR coils;
   adaptively determining an index gauge for at least one k-space data line acquired for each coil;
   comparing the index gauges; and
   automatically selecting/deselecting, based on the index gauge comparison, a number of MR coils to activate for image data acquisition.

2. The method of claim 1 wherein the steps of adaptively determining and automatically selecting are performed without user input parameters and hardware markers.

3. The method of claim 1 wherein the adaptively determining step is further defined as extracting a relative intensity of each coil from the acquired k-space data.

4. The method of claim 2 wherein the MR coils are phased array coils and further comprises the steps of:
   selecting a desired FOV;
   determining a relative position of each phased array coil with respect to the desired FOV; and
   activating the phased array coils most sensitive in the desired FOV.

5. The method of claim 1 wherein the MR coils are phased array coils and wherein the index gauge is an intensity value of at least one k-space data line acquired in the fast prescan for each coil, and further comprises:
   arranging the intensity values for the k-space data lines into an intensity profile;
   selecting a number of phased array coils to activate during final image data acquisition from the intensity profile; and
   acquiring imaging data during the final imaging data acquisition from only the phased array coils selected.

6. The method of claim 1 wherein the index gauge is determined by finding a total intensity of each image, which is proportional to, and found by, integrating a coil sensitivity profile weighted by a spin density of a scanning object over a desired FOV.

7. The method of claim 1 wherein the step of adaptively determining an index gauge further comprises the step of determining a coil position explicitly.

8. The method of claim 7 wherein the step of determining coil position explicitly, includes determining whether any coil is positioned at least partially outside a desired FOV relative to positions of a number of coils within the desired FOV.

9. The method of claim 7 wherein the coil position is determined by one of:
   projecting an intensity of the k-space data onto an axis of the MR coils and conducting a profile fit;
   calculating a center of mass of an intensity profile; and
   determining a peak location of the intensity profile along an axis of the MR coils.

10. The method of claim 1 wherein the step of initializing a fast prescan and acquiring k-space data includes obtaining only a central portion of k-space data to determine a total intensity of each image as the index gauge.

11. The method of claim 1 wherein the index gauge ($G_i$) is determined by approximating a constant spin density according to:

$$G_i = \sum_{(x,y)} |S_i(x,y)M(x,y)| \approx M_o \sum_{(x,y)} |S_i(x,y)|,$$

where $S_i(x,y)$ is a spatial sensitivity of an i-th MR coil of an N-coil phased coil array, and $M(x,y)$ is a spin magnetization density weighted by an imaging sequence, $M_o$ is the approximated constant spin density, and where the summation is over all spatial pixels in a desired FOV.

12. The method of claim 1 wherein the index gauge ($G_i$) is determined without assuming a constant spin density according to:

$$G_i = \sum_{(x,y)} \left( |I_i(x,y)| / \sum_i |I_i(x,y)| \right) = \sum_{(x,y)} \left( |S_i(x,y)| / \sum_i |S_i(x,y)| \right)$$

where $S_i(x,y)$ is a spatial sensitivity of an i-th MR coil of an N-coil phased coil array, $I_i(x,y)$ is a total intensity obtained from central k-space data for each MR coil, and wherein the summation is over all spatial pixels in a desired FOV.

13. The method of claim 1 wherein the step of comparing includes determining a threshold on-the-fly for evaluating the data acquired from each coil and eliminating a coil with a least SNR, wherein the threshold is determined based only on the index gauges for each of the coils.

14. A computer program having a set of instructions that when executed by a computer causes the computer to:
   analyze prescan data acquired from activating a number of phased array coils during a preliminary MR scan;
   extract a relative intensity of each coil from the prescan data; and
   determine, from the relative intensity of each coil, a number of phased array coils to activate to acquire reconstruction imaging data during a reconstruction imaging scan.

15. The computer program of claim 14 wherein the determination act includes on-the-fly calculation of a threshold value from the relative intensity of each coil to eliminate at least one coil with a lowest relative intensity.

16. The computer program of claim 14 wherein the set of instructions further causes the computer to:
   profile the relative intensity for each coil onto a map of a phased array coil assembly having a plurality of phased array coils capable of acquiring the prescan data; and
   activate those phased array coils most sensitive to an imaging FOV.

17. The computer program of claim 14 wherein the set of instructions further causes the computer to activate for image reconstruction those phased array coils that produce a relative intensity having a value greater or equal to an intensity threshold value.

18. The computer program of claim 17 wherein the intensity threshold value includes a mean of the data frame intensity values.

19. The computer program of claim 14 wherein the set of instructions further causes the computer to integrate a coil sensitivity profile weighted by a spin density of a scanning subject over a field-of-view for each phased array coil to determine the relative intensity of each coil.

20. The computer program of claim 14 wherein the prescan data from a phased array coil includes an intermediate image which is represented by:

$$I_i(x,y) = S_i(x,y) M(x,y)$$

where:
$I_i(x,y)$ is the prescan data of an i-th phased array coil;
$S_i(x,y)$ represents a spatial sensitivity of the i-th phased array coil; and
$M(x,y)$ represents a spin density of a scanning subject within a desired field-of-view.

21. The computer program of claim 20 wherein the relative intensity is represented as an index gauge ($G_i$) and is determined by:
approximating a constant spin density according to:

$$G_i = \sum_{(x,y)} |S_i(x,y) M(x,y)| \approx M_o \sum_{(x,y)} |S_i(x,y)|,$$

where $S_i(x,y)$ is a spatial sensitivity of an i-th MR coil of an N-coil phased coil array, and $M(x,y)$ is a spin magnetization density weighted by an imaging sequence, $M_o$ is the approximated constant spin density, and where the summation is over all spatial pixels in a desired FOV.

22. The computer program of claim 20 wherein the relative intensity is represented as an index gauge ($G_i$) and is determined by without assuming a constant spin density according to:

$$G_i = \sum_{(x,y)} \left( |I_i(x,y)| / \sum_i |I_i(x,y)| \right) = \sum_{(x,y)} \left( |S_i(x,y)| / \sum_i |S_i(x,y)| \right)$$

where $S_i(x,y)$ is a spatial sensitivity of an i-th MR coil of an N-coil phased coil array, $I_i(x,y)$ is a total intensity obtained from central k-space data for each MR coil, and wherein the summation is over all spatial pixels in a desired FOV.

23. The computer program of claim 14 wherein the relative intensity is extracted by the computer program according to one of:
projecting an intensity of the k-space data onto an axis of the MR coils and conducting a profile fit;
calculating a center of mass of an intensity profile; and
determining a peak location of the intensity profile along an axis of the MR coils.

24. An MRI apparatus comprising:
a magnetic resonance imaging (MRI) system having a plurality of gradient coils positioned about a bore of a magnet to impress a polarizing magnetic field and an RF transceiver system and an RF switch controlled by a pulse module to transmit RF signals to a phased array coil assembly to acquire MR images; and
a computer programmed to:
initialize a fast MR scan using a plurality of coils in the phased array coil assembly;
acquire fast scan imaging data of a desired FOV wherein the fast scan imaging data includes at least one k-space line of data for each of the plurality of coils in the phased array coil assembly;
determine a relative position of each of the plurality of coils with respect to the desired FOV based only on the at least one k-space line of data; and
select and initialize only a number of coils from the plurality of coils for image acquisition and reconstruction based on the relative positions of each coil to optimize SNR in the desired FOV.

25. The MRI apparatus of claim 24 wherein the computer is further programmed to:
determine an intensity value for at least one k-space line of data for each of the plurality of coils;
determine a coil sensitivity value for each of the plurality of coils from the intensity value of each k-space line of data; and
determine coil position relative to the desired FOV from the coil sensitivity values.

26. The MRI apparatus of claim 25 wherein the computer is further programmed to reject at least sensitive coil in the desired FOV for image reconstruction.

27. The MRI apparatus of claim 25 wherein the computer is further programmed to:
identify coils most sensitive to the desired FOV by comparing a sensitivity value for each coil to a sensitivity threshold value, and
to select only the coils that have sensitivity values that are equal to or greater than the sensitivity threshold value for image data acquisition.

28. The MRI apparatus of claim 25 wherein the computer is further programmed to:
create an intensity profile that includes a projection of each intensity value onto a map of the plurality of coils; and
determine a center of mass of the intensity profile to locate a relative position of each coil.

29. The MRI apparatus of claim 24 wherein the computer is further programmed to calculate an index gauge ($G_i$) to adaptively determine the relative position of the plurality of coils.

30. The MRI apparatus of claim 29 wherein the computer is further programmed to calculate the index gauge ($G_i$) according to one of:
by approximating a constant spin density according to:

$$G_i = \sum_{(x,y)} |S_i(x,y) M(x,y)| \approx M_o \sum_{(x,y)} |S_i(x,y)|,$$

where $S_i(x,y)$ is a spatial sensitivity of an i-th MR coil of an N-coil phased coil array, and $M(x,y)$ is a spin magnetization density weighted by an imaging sequence, $M_o$ is the approximated constant spin density, and where the summation is over all spatial pixels in a desired FOV; and $$G_i = \sum_{(x,y)} \left( |I_i(x,y)| / \sum_i |I_i(x,y)| \right) = \sum_{(x,y)} \left( |S_i(x,y)| / \sum_i |S_i(x,y)| \right)$$

where $S_i(x,y)$ is a spatial sensitivity of an i-th MR coil of an N-coil phased coil array, $I_i(x,y)$ is a total intensity obtained from central k-space data for each MR coil, and wherein the summation is over all spatial pixels in a desired FOV.

31. The MRI apparatus of claim 25 wherein the computer is programmed to determine a relative position of each of the plurality of coils on-the-fly and without a lookup table by finding a total mean value of an index gauge for each coil.

32. An MRI device for improved image reconstruction comprising:

means for initializing a fast prescan and acquiring k-space data that includes at least one k-space data line for each of a plurality of MR coils;

means for determining an index gauge for at least one k-space data line acquired for each coil;

means for comparing the index gauges dynamically; and means for automatically selecting/deselecting a number of MR coils to activate for image data acquisition based on the comparison.

* * * * *